United States Patent [19]

Gray et al.

[11] 4,235,454
[45] Nov. 25, 1980

[54] STABILIZATION SYSTEM FOR A MEDICAL DIAGNOSTIC DEVICE

[75] Inventors: Floyd L. Gray, Hales Corner; Jerome H. Adam, Waukesha; Larry Susami, Wauwatosa; Rick A. Zamzow, Waukesha, all of Wis.

[73] Assignee: General Electric Company, Milwaukee, Wis.

[21] Appl. No.: 957,530

[22] Filed: Nov. 3, 1978

[51] Int. Cl.³ .............................................. B60S 9/18
[52] U.S. Cl. .................................. 280/766; 180/214; 250/363 S; 254/86 R; 280/43.2
[58] Field of Search ............... 280/766, 764, 765, 767, 280/79.1 A, 43.2, 43.23, 43.24, 43.17, 763; 180/24.02, 209, 214, 212; 254/86 R, 86 H, 87; 250/363 S; 212/145

[56] References Cited

U.S. PATENT DOCUMENTS

| 1,346,915 | 7/1920 | Sauvage | 180/214 |
| 2,546,491 | 3/1951 | Bill | 280/43.2 |
| 2,879,075 | 3/1959 | Wallace | 280/43.2 |
| 3,011,057 | 11/1961 | Anger | 250/363 S |
| 3,221,731 | 12/1965 | Annis et al. | 250/363 S |
| 3,658,377 | 4/1972 | Behrmann | 296/179 |
| 3,700,059 | 10/1972 | Sutton | 280/43.2 |

Primary Examiner—David M. Mitchell
Attorney, Agent, or Firm—Douglas E. Stoner; Dana F. Bigelow

[57] ABSTRACT

A mobile medical diagnostic device having a mobility chassis with two supporting wheels and a central steerable drive wheel. The device has an electrical power steering system controlled by two synchronized handles operable by wrist action of an operator walking behind the device. The handles include a rotatable grip for controlling the velocity of the device. Advancing the grip actuates the throttle to the drive wheel and retarding the grip actuates a proportional electromechanical braking system. The device includes a proximity detector system which uses ultrasonic transducers to determine when an obstacle is within close proximity to the device, and to responsively and automatically actuate the brake system. The device has a stabilization system which automatically extends an outboard support on each side of the central wheel when the device is positioned for diagnostic analysis and automatically retracts the supports to facilitate mobility of the device.

8 Claims, 5 Drawing Figures

STABILIZATION SYSTEM FOR A MEDICAL DIAGNOSTIC DEVICE

RELATED CASES

A steering and throttling system for a mobile device is claimed in copending U.S. application Ser. No. 957,532, filed Nov. 3, 1978 and assigned to the same assignee as the present invention. A braking system for a mobile device is claimed in copending U.S. application Ser. No. 957,533, filed Nov. 3, 1978 and assigned to the same assignee as the present invention. A proximity detector system for a mobile device is claimed in U.S. application Ser. No. 957,531, filed Nov. 3, 1978 and assigned to the same assignee as the present invention.

BACKGROUND OF THE INVENTION

The present invention relates generally to a stabilization system for a device having a self-propelled chassis. More particularly, the invention relates to a stabilization system for a mobile medical diagnostic device which requires stabilization of the device during analysis of a patient.

Various types of equipment are made mobile by mounting the equipment on a self-propelled chassis. Mobility is particularly significant for medical diagnostic equipment, such as an X-ray device and a scintillation camera device for obtaining diagnostic images of a patient. In many cases, the patient requires intensive care or critical care and cannot be moved, so the diagonostic device must be transported to the patient. The device may be required to be operated virtually anywhere in the hospital. The device must maneuver along extremely long corridors, around life support systems and around monitoring systems or traction devices. The device must also move in and out of elevators, through doorways, up wheelchair ramps, over carpeting and tile, and across small open thresholds.

A problem is presented by the mobilization of scintillation camera equipment equipment which is used to detect gamma ray photons emitted from a body in which a radioisotope has been infused to produce a diagnostic image of the patient. Scintillations occur where photons are absorbed by crystalline material. The scintillations are received by a detector head which contains scintillation crystals, photomultiplier tubes and lead shielding. A typical system is based on the camera of Anger, as disclosed in U.S. Pat. No. 3,011,057, and is herein incorporated by reference. The detector head, along with the suspension arm, weighs approximately 300 pounds. The suspension system and column for the detector head add more weight along with the very high density of electronic instrumentation used to analyze and display the diagnostic images of the patient. The substantial size and weight of the diagnostic equipment requires a similarly substantial chassis and mobility drive system to transport the equipment. The combined equipment and mobility chassis weighs over 2,000 pounds and presents the problem of safely maneuvering, steering and braking the device while it is being moved and then stabilizing the device once it is in position.

Typical mobility chassis of the prior art use conventional four-wheeled system which provides a good stable base when the device is stationary in a desired location. However, the four-wheeled system has a relatively large turning radius and is not as maneuverable as would be desired. A three-wheeled system, having a central steerable wheel has a relatively tight turning radius and is extremely maneuverable. A particular problem with the mobile maneuverable three-wheeled system is presented once the device is relocated and positioned for analysis of the patient. The heavy detector is extended to the side of the device and the three-wheeled system does not provide a sufficiently stable base for the device.

Accordingly, one object of the present invention is to provide a mobile medical diagnostic device which is extremely compact and which is maneuverable within a hospital.

Another object is to provide a diagnostic device which is extremely maneuverable while mobile and which is extremely stable while positioned for analysis of a patient.

SUMMARY OF THE INVENTION

The invention is directed to an automatic stabilization system for a mobile medical diagnostic device, such as scintillation camera equipment, which can be quickly and safely maneuvered within a hospital. In the scintillation camera example, the chassis for the device includes two longitudinal sides, two forward support wheels and a single central steerable wheel assembly at the rear of the device. The central rear wheel is also the drive wheel having a bidirectional variable speed electric motor adapted as a means for self-propelling the device. The device is controlled by twin synchronized handles located approximately waist high at the rear of the device and adapted to readily respond to wrist action of an operator walking behind the device. The device has a movable detector head which rests on a support during mobility of the device and which is raised and extended during stationary diagnostic analysis of a patient.

In accordance with the present invention, two extendable supports are located on opposite sides of the single support wheel near the longitudinal sides of the device. Each extendable support includes a lead screw having a confined drive nut which advances and retracts the support. A bidirectional motor is coupled to each drive nut. The system includes circuitry means for automatically actuating the motor to extend the supports to the supporting surface when the dectector head is raised from the support to provide a stabilized base for the device during analysis. Circuitry means is also provided for automatically actuating the motor to retract the supports when the detector head is returned to the support to facilitate mobility of the device.

BRIEF DESCRIPTION OF THE DRAWINGS

While the novel features of the invention are set forth with particularity in the appended claims, the invention will be understood along with other features thereof from the following detailed description taken in conjunction with the drawings in which:

DETAILED DESCRIPTION OF THE DRAWINGS

Figure 1:
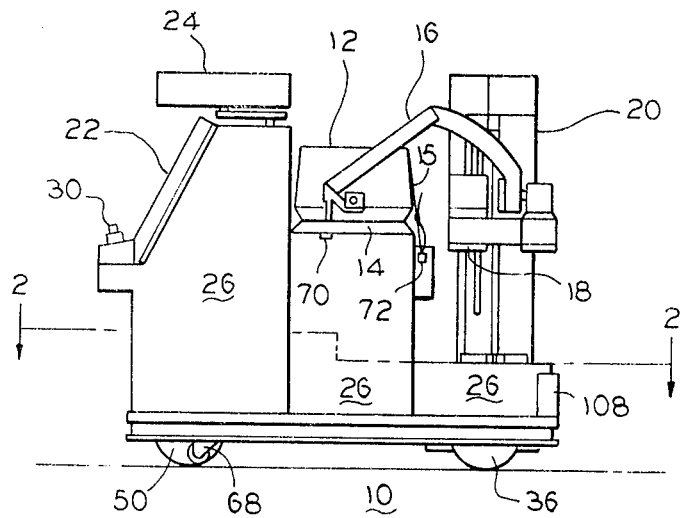
FIG. 1 is a side elevation view of a mobile scintillation camera device incorporating a stabilization system.

Referring first to FIG. 1, there is shown a mobile scintillation camera device 10 in position for being moved within a hospital. The detector head 12 contains the scintillation crystals, photomultiplier tubes and lead shielding for receiving gamma ray energy. During analysis, the detector head 12 is positioned over the patient; however, the detector head is shown in the transportable position resting on a support pad 14 and secured by a hold down strap 15. The detector head 12 is supported by a suspended arm 16 cantilevered from a suspension system indicated by numeral 18. The suspension system 18 is contained within a vertical column structure 20 and controls the vertical position of the detector head 12 at desired positions along the vertical column structure. A control console 22 contains camera electronics, imaging oscilloscopes, and controls for accessory equipment the for data analysis. The diagnostic image from the patient is normally displayed at persistance oscilloscope 24. Enclosed within housings 26 (but not shown) are a counterpoise and rotation system for column 20, the storage batteries for providing d.c. power, and all of the electronics and circuitry for the equipment and mobility for the device. The device 10 utilizes conventional 115 volt a.c. power for detection, imaging and data processing during analysis of the patient and utilizes the storage batteries for d.c. power for the mobility systems used to maneuver the device to desired locations within the hospital. The mobility controls are located approximately waist high at the rear of the device. The controls include a right handle assembly 30 and a left handle assembly 32 which are synchronized so that the device can be controlled by either or both hands of the operator.

Figure 2:
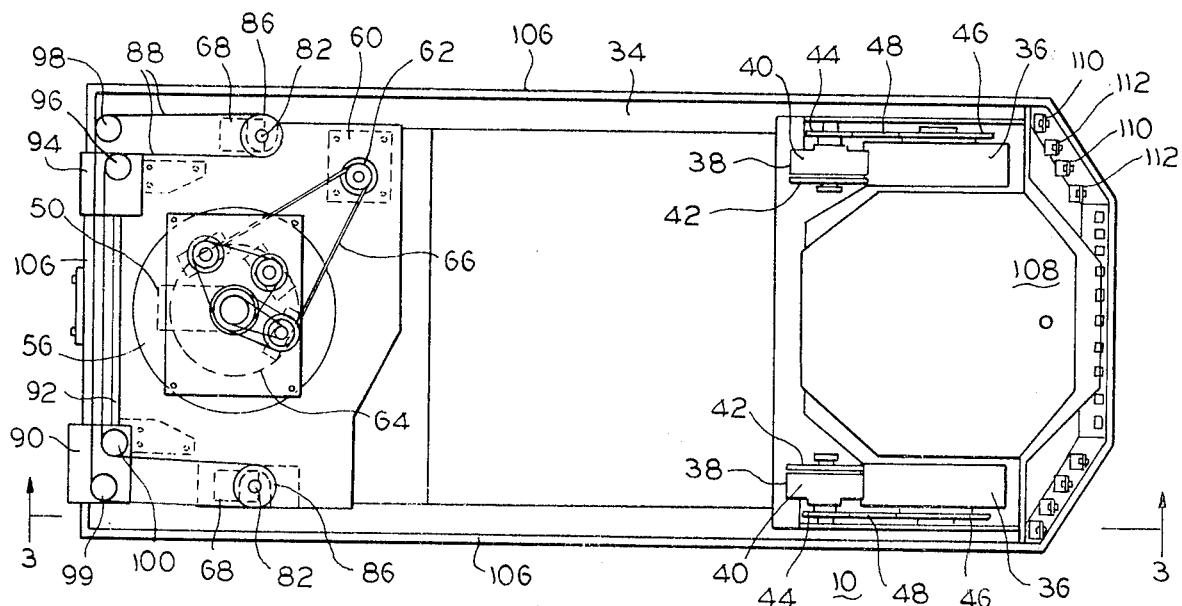
FIG. 2 is a sectional view of the chassis of the device taken along line 2—2 of FIG. 1.
Figure 3:
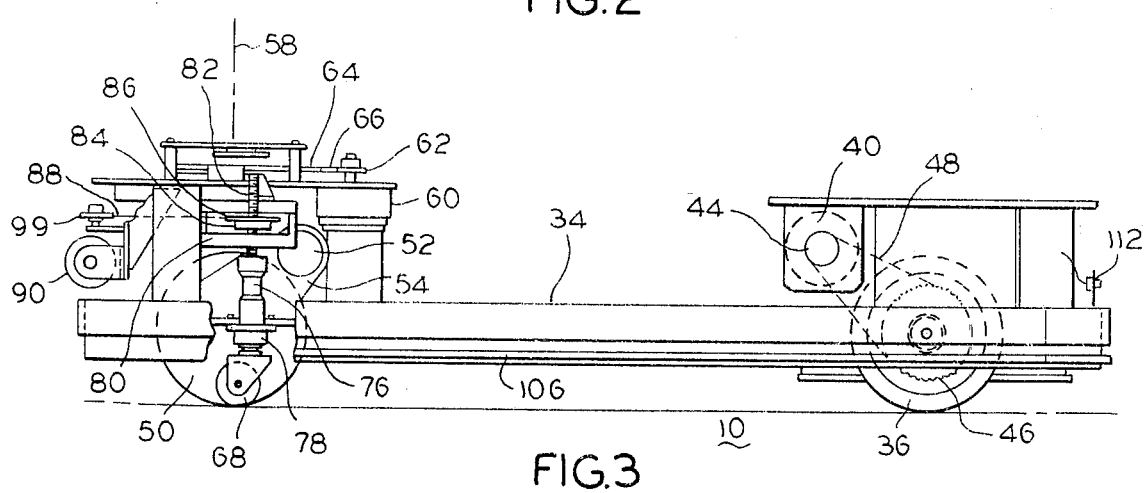
FIG. 3 is a sectional view of the chassis taken along line 3—3 of FIG. 2.

Referring now to FIGS. 2 and 3, there are shown the features of the chassis mobility systems. The mobility systems are supported by and attached to a rectangular frame 34 surrounding the device 10. The front of the device is supported by two wheel assemblies 36 attached by conventional bearing housings to frame 34. The primary braking system for the device is provided by proportional electromechanical brakes 38. The brakes 38 utilize an electromagnetic coil within a housing 40 and an engagable magnetic disc 42 having an abrasive surface. The amount of engagement by the disc 42 and housing 40 is proportional to the amount of current applied to the electromagnetic coil. The brakes 38 are connected by brake sprockets 44 to wheel sprockets 46 by a continuous chain 48.

The rear of the device 10 is supported by a central, steerable wheel assembly 50. The three-wheeled mobility system permits the device to be extremely maneuverable. In this example, the central wheel assembly 50 is also the drive wheel having means for self-propelling the device 10. The self-propelling means is provided by a bi-directional variable speed motor 52 coupled to the wheel assembly 50 by a conventional gear drive 54. The wheel assembly and self-propelling means are mounted to a rotatable bearing platform 56 having a vertical axis of rotation 58 and mounted to frame 34. The steerable wheel assembly 50 is coupled to a bi-directional steering motor 60 by a steering drive sprocket 62 and a steering wheel sprocket 64 connected by a continuous chain 66.

Several features of the device are described having sprocket and chain drive systems. It should be understood that various gear trains or belt drive systems could be employed in alternative embodiments.

The three-wheeled mobility system provides a very compact and maneuverable system for controlling and transporting the device. However, when the scintillation camera is positioned for analysis and the heavy detector head 12 is extended to the side of the device over the patient, the three-wheeled mobility system does not provide a sufficiently stable support for the device. In order to provide a more stable support for the device during diagnostic analysis, a stabilization system 67 is provided having extendable casters 68 at the longitudinal sides near the rear corners of the device. The casters are extendable to the supporting surface which is usually the floor of the hospital. The stabilization system is automatically actuated when an a.c. power cord of the device 10 is plugged into a wall outlet and the hold down strap is released prior to lifting the detector head 12 from the support pad 14. A sensing microswitch 72 is provided at the end of the detector head hold down strap 15 (as shown in FIG. 1) which will open to indicate that the detector head is not secured to the support pad and to actuate the system.

Figure 4:
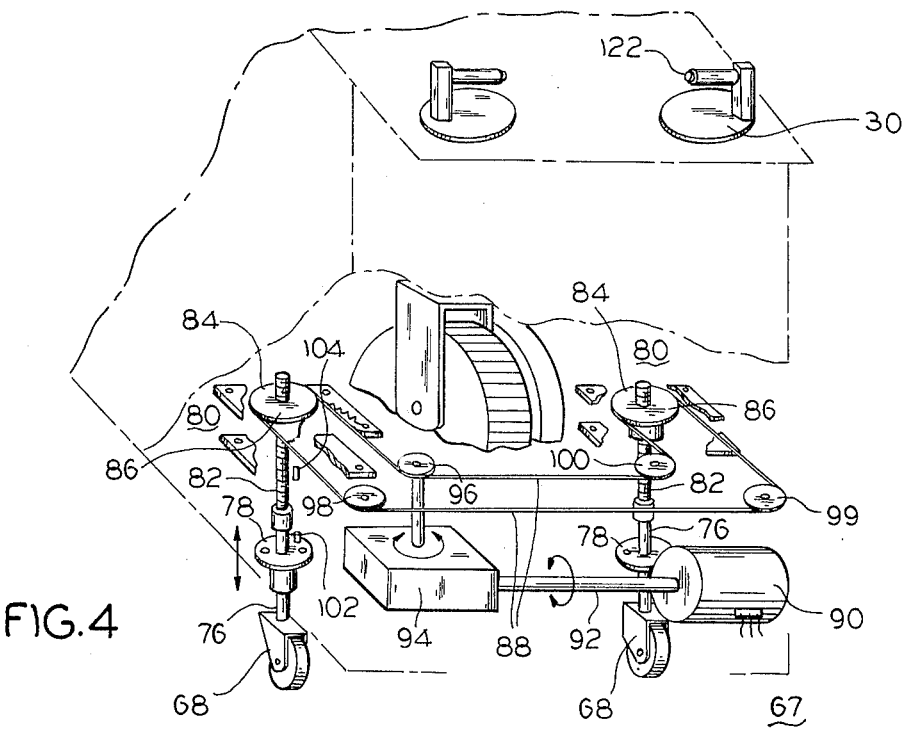
FIG. 4 is a cutaway perspective view showing the mechanical elements of the stabilization system.
Figure 5:
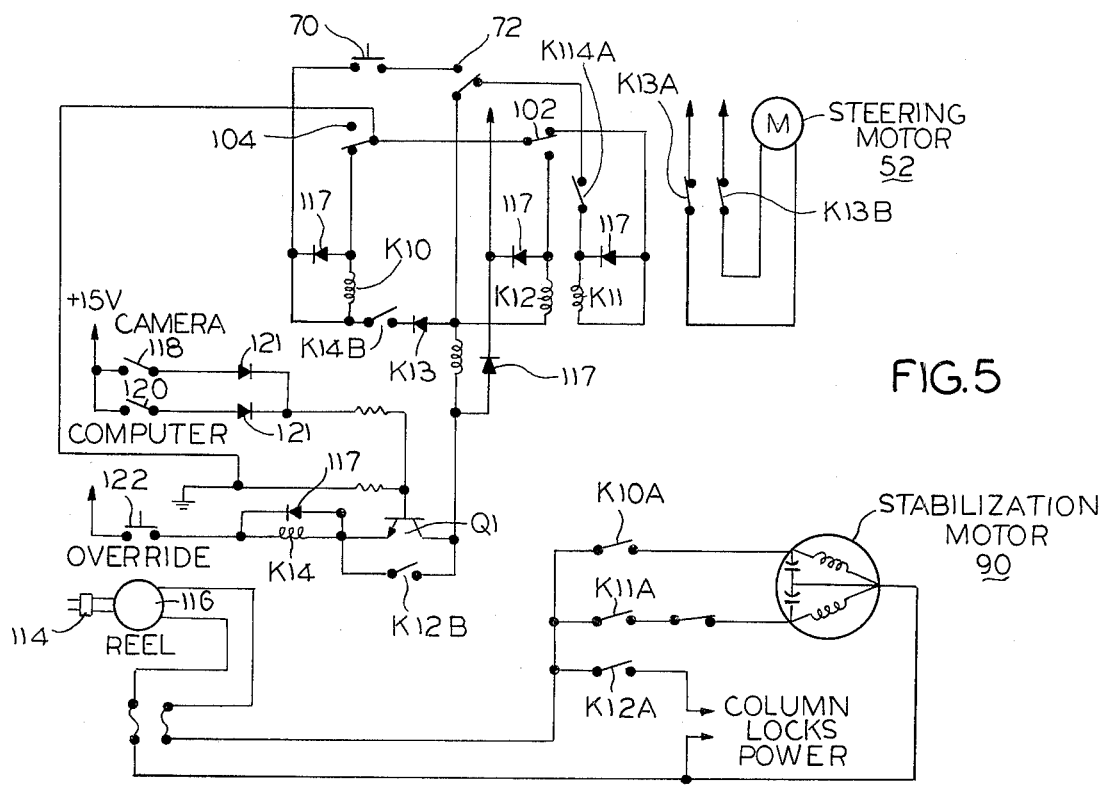
FIG. 5 is a schematic diagram of the circuitry for the stabilization system.

Referring also to FIGS. 4 and 5, the details of of the stabilization can be fully described. The casters 68 have vertical shafts 76 which are slideable through bearing journals 78 attached to frame 34. Each caster drive assembly 80 includes a lead screw 82 driven by a confined rotatable nut 84, which is rotated clockwise or counterclockwise by a sprocket 86 and a continuous chain 88. The stabilization system is operated by a bidirectional, split-phase stabilization motor 90 having an output shaft 92 coupled to a gear box 94. The gear box 94 has a drive gear sprocket 96 coupled to the continuous chain 88. Idler sprockets 98, 99 and 100 are provided to synchronize the two caster drive assemblies 80 to the drive gear sprocket 96. During operation, when the device is plugged into a wall outlet and the hold down strap 15 is removed, circuitry is provided such that stabilization motor 90 will automatically operate to drive gear sprocket 96. Drive gear sprocket 96 will rotate the continuous chain 88, thereby rotating the confined nuts 84 which drive the lead screws downward and extend casters 68 until a lower limit switch 102 is actuated by the left assembly 80. At this time the central steerable wheel assembly is raised from the floor and the device is supported by the two front wheels 36 and the two rear stabilizing casters 68. Similarly, when the hold down 15 is secured, the circuitry will again activate the motor 90 in the opposite direction, whereby the casters will be retracted until an upper limit switch 104 has been actuated and the stabilization system will again come to rest.

FIG. 5 shows the circuit diagram of the stabilization system with all switches shown in the deactivated position. The circuit will be briefly described where an a.c. power cord 114 having a take-up reel 116 is plugged into a wall outlet with the detector head 12 resting on the support pad and having the hold down strap secured around the detector head (as shown in FIG. 1). Under the above condition, the tape switch 70, located under the support pad, and the microswitch 72, located at the end of the hold down strap, are closed and the unit is ready to be unplugged and moved. The switches 70 and 72 complete a circuit which energize a relay coil K10 and automatically retracts the stabilizing casters 68. Each relay coil in the circuit includes a transient suppression diode 117 in parallel with the relay. The relay K10 operates a contact switch K10A which supplies a.c. power to the stabilization motor 90 and causes rotation in one direction. The motor rotates drive gear 96 and the casters 68 are moved upward until the left assembly actuates the upper limit switch 104. The upper limit switch 104, when actuated, removes the ground connection from relay coil K10 which de-energizes the relay and opens switch K10A which stops the motor 90. The device is then unplugged and is ready to be moved.

When the device has been repositioned and is again ready for stationary analysis of a patient, the hold down strap is removed which initiates the automatic extension of the supports. When the hold down strap is removed, the microswitch 72 opens, which disconnects power from relay K10 and applies power to relay coil K11. The relay coil K11 operates a contact switch K11A and supplies a.c. power to rotate the motor 90 in the opposite direction. The motor rotates drive gear 96 in the opposite direction and moves the casters 68 downward. The casters continue downward until the left assembly actuates the lower limit switch 102. The lower limit switch 102, when actuated, removes the ground connection from relay coil K11 which de-energizes the relay and opens switch K11A which stops the motor.

The circuit provides additional features which facilitate the safe operation of the device. It is desirable to disable the steering system and to energize suspension column locks of the device when the device is positioned for analysis. It is also desirable to disable power to the steering motor whenever the scintillation camera or the computer of the device is being operated. When the lower limit switch 102 is actuated, it also applies power to a relay coil K12. Relay K12 operates a contact switch K12A which applies power to the column lock of the device, and also operates contact switch K12B. Switch K12B energizes relay coil K13 to operate contact switches K13A and K13B which disconnect power to the steering motor 52. When either a camera switch 118 or a computer switch 120 is turned on, 15 volts are applied through gating diodes 121 to the base of a transistor Q1. The transistor Q1 grounds relay K13 which also opens switches K13A and K13B which disconnect power to the steering motor. When both switches 118 and 120 are turned off, the transistor Q1 is turned off and relay K13 is only actuated by the lower limit switch 102 as previously discussed.

On some occasions it may be necessary to override the "automatic system" and raise the casters. An "override" switch 122 is provided in the steering handle assembly. When the override switch is pressed, power is applied to a coil relay K 14, which opens contact switch K114A and closes contact switch K14B. When switch K114A opens, power is disconnected from relay K11. With K11 de-energized, there is no further downward movement of the casters. When switch K14B closes, power is applied to relay K10. Relay K10 then produces upward caster movement until the upper limit switch 104 is reached as previously described. Pushing the override switch causes the casters to raise immediately for emergency travel, regardless of the position of the detector head.

In alternative embodiments, the supports could have large flat bearing surfaces rather than rotatable casters. However, the casters provide additional advantages to the system. In an extreme emergency, the casters permit the device to be immediately rolled away from the bedside of the patient. Also, if the steering or propelling motor were to be inoperable for any reason, the stabilizing caster could be extended and permit the device to be relocated by an external means.

In other alternative embodiments, the supports could be actuated by other hydraulic or mechanical systems to stabilize the device.

In conclusion, a stabilization system has been provided for a mobile device which allows the device to have the maneuverability of a three-wheeled system during movement of the device while having a wide, stable four-wheeled base while the device is in a stationary position.

While a specific embodiment of the present invention has been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. A stabilization system for a mobile medical diagnostic device having a movable detector head that is raised in preparation for diagnostic analysis and is lowered and secured in preparation for mobile movement and having two longitudinal sides and being supported by wheel assemblies on a supporting surface, said system comprising:
    at least one extendable support located near one of the longitudinal sides of the device,
    means for automatically extending said at least one extendable support to the supporting surface when the detctor head is not secured, and
    means for automatically retracting said support to facilitate mobility of the device when said detector head is lowered and secured.

2. The stabilization system as recited in claim 1 wherein said at least one extendable support is extendable in a generally vertically outboard direction.

3. The stabilization system as recited in claim 1 wherein one of said at least one extendable support is located near each of the two longitudinal sides of the device.

4. A stabilization system for a mobile medical diagnostic device having a movable detector head that is raised in preparation for diagnostic analysis and is lowered and secured in preparation for mobile movement and having two longitudinal sides and two supporting wheels at one end and a single central wheel at the other end with all wheels adapted to be supported on a supporting surface, said system comprising:
    two extendable supports located on opposite sides of the single support wheel near the longitudinal sides of the device,
    means for automatically extending said supports to the supporting surface when the detector head is not secured, and
    means for automatically retracting said supports to facilitate mobility of the device when the detector head is lowered and secured.

5. The stabilization system as recited in claims 1 or 4 wherein said extending and retracting means comprise a lead screw cooperating with each of said extendable supports and said lead screw having a confined drive nut coupled to a means for rotating said drive nut for extending and retracting said lead screw.

6. An automatic stabilization system for a mobile medical diagnostic device having a moveable detector head which rests on a support and is secured during mobility of the device and which is unsecured and raised from the support during diagnostic analysis, and the device having two longitudinal sides and two supporting wheels at one end and a single central wheel at the other end and supported on a supporting surface, comprising:
- two extendable supports, each located on opposite sides of the single support wheel near the longitudinal sides of the device,
- means for automatically extending said supports to the supporting surface when the detector head is not secured to the detector support, and
- means for automatically retracting said supports when the detector head rests on the support and is secured.

7. The stabilization system as recited in claim 6 wherein said automatically extending means and said automatically retracting means further comprises:
- a lead screw cooperating with each of said extendable supports;
- a confined drive nut adapted to receive said lead screw;
- a motor coupled to said confined drive nut;
- a support switch on the detector support which is actuated by the detector head;
- a first relay which is electrically connected to said support switch and said motor for actuating said motor such that said supports are extended when the detector head is off of the detector support;
- a lower limit switch connected to said first relay which acts to stop said motor when said support is fully extended;
- a second relay which is electrically connected to said support switch and said motor for actuating said motor such that said supports are contracted when the detector head is on the detector support;
- an upper limit switch connected to said second relay which acts to stop said motor when said support is fully contracted.

8. The stabilization system as recited in claims 1, 4 or 6 wherein each of said supports includes a rotatable caster which is extendable to the supporting surface.

* * * * *